United States Patent [19]

Digenis et al.

[11] Patent Number: 5,380,523

[45] Date of Patent: Jan. 10, 1995

[54] HIGH ENERGY COPRECIPITATE OF NONOXYNOL OLIGOMER, PVP AND IODINE HAVING CONTRACEPTIVE AND POTENT ANTI-HIV PROPERTIES

[75] Inventors: George A. Digenis, Lexington, Ky.; Alexander G. Digenis, Nashville, Tenn.

[73] Assignee: University of Kentucky Research Foundation, Lexington, Ky.

[21] Appl. No.: 106,948

[22] Filed: Aug. 17, 1993

[51] Int. Cl.$^6$ .................... A61K 47/32; A61K 31/085

[52] U.S. Cl. .................... 424/78.25; 424/DIG. 14; 514/843; 514/967

[58] Field of Search ......... 424/78.24, 78.25, DIG. 14; 514/967, 843

[56] References Cited

U.S. PATENT DOCUMENTS

| | | |
|---|---|---|
| 4,297,341 | 10/1981 | Waller et al. . |
| 4,299,759 | 11/1981 | Miyata et al. . |
| 4,317,447 | 3/1982 | Williams . |
| 4,707,362 | 11/1987 | Nuwayser . |
| 4,775,638 | 10/1988 | Haisma . |
| 4,923,677 | 5/1990 | Simon et al. .................... 422/37 |
| 4,925,033 | 5/1990 | Stoner . |
| 4,954,351 | 9/1990 | Sackler et al. . |
| 5,070,889 | 12/1991 | Leveen et al. . |
| 5,073,365 | 12/1991 | Katz et al. . |
| 5,156,164 | 10/1992 | Le Veen et al. . |

OTHER PUBLICATIONS

Benes, S. et al. "Inhibition of Growth of *Chlamydia trachomatis* by Nonoxynol-9 in Vitro", *Antimicrob. Agent Chemother.*, (1985) 27:724-726.

Kelly, J. P. et al. "In Vitro Activity of the Spermicide Nonoxynol-9 Against *Chlamydia trachomatis*", *Antimicrob. Agent Chemother*, (1985) 27:760-762.

Austin, H., et al. "A Case-Control Study of Spermicides and Gonorrhea", *JAMA* (1984) 251:2822-2824.

Singh, B. et al. "Studies on the Development of a Vaginal Preparation Providing both Prophylaxis Against Venereal Disease and Other Genital Infections and Contraception: Effect in Vitro of Vaginal Contrceptive and Non-Contraceptive Preparations on Treponema Pallidum and Neisseria Gonorrhoeae", *Br. J. Vener. Dis.* (1972) 48:57-64.

Asculai, S. S. et al. "Inactivation of Herpes Simplex Viruses by Nonionic Surfactants", *Antimicrob. Agent Chemother.* (1978) 13:686-690.

Hicks, D. R. "Inactivation of HTLV-III/LAV-Infected Cultures of Normal Human Lymphocytes Nonoxynol-9 in Vitro", *Lancet* (1985) 1422-1423.

Friedman-Kein, A. E. "Treatment of Recurrent Genital Herpes with Topical Alpha Interferon Gel Combined with Nonoxynol 9", *J. Am. Acad. Dermol.* (1986) 15:989-994.

Voeller, B. "Nonoxynol-9 and HTLV-III", *Lancet* (1986) 1153.

Malkovsky, M. et al. "Inactivation of HIV by Nonoxynol-9", *Lancet* (1988) 645.

Liebert, M. A. "Final Report on the Safety Assessment of nonoxynols -2, -4, -8, -9, -10, -12, -14, -15, -30, -40, and -50", *J. Am. Coll. Toxicol.* (1983) 2;35-60.

Chvapil, M. et al. "Studies on Nonoxynol-9. III. Effect on Fibroblasts and Spermatozoa", *Fertil. Steril.* (1980) 33:521-525.

Knaak, J. B. et al. "Excretion of Certain Polyethylene Glycol Ether Adducts of Nonylphenol by the Rat", *Toxicol. Appl. Pharmacol.* (1966) 9:331-340.

(List continued on next page.)

*Primary Examiner*—Thurman K. Page
*Assistant Examiner*—Peter F. Kulkosky
*Attorney, Agent, or Firm*—Lowe, Price, LeBlanc & Becker

[57] ABSTRACT

A composition which is a contraceptive with potent anti-HIV activity. The composition is a high energy coprecipitate of nonoxynol-9 oligomers, polyvinylpyrrolidone (PVP) and iodine or PVP-I and shows a pronounced synergistic, anti-HIV effect between the compounds of the composition. A method of obtaining a contraceptive and anti-HIV environment in a female comprising administering to said female an effective amount of a high energy coprecipitate.

18 Claims, No Drawings

OTHER PUBLICATIONS

Walter, B. A. et al. "Disposition of [$^{14}$C] Nonoxynol-9 After Intravenous or Vaginal Administration to Female Sprague-Dawley Rats", *Toxicol. Applied Pharmacol.* (1988) 96:258–268.

Walter, B. A. et al. "High-Performance Liquid Chromatographic (HPLC) Analysis of Oligomeric Components of Spermicide Nonoxynol-9", *Pharm. Res.* (1991) 8:409–411.

Walter, B. A. et al. "Solubilization and in Vitro Spermicidal Assessment of Nonoxynol-9 and Selected Fractions Using Rabbit Spermatozoa", *Pharm. Res.* (1991) 8:403–408.

Higuchi, W. I. et al. "Drug Membrane Transport Enhancement Using High Energy Drug-Povidone Coprecipitates", *Proceedings of the International Symposium on Povidione,* Digenis, G. A. and Ansell, J., Eds. Lexington, (1983) pp. 71–79.

Simonelli, A. P. et al. "Preparation and Evaluation of High Energy PVP-Coprecipitates Including Reversion Phenomena", *Proceedings of the 2nd International Symposium on Povidone,* Digenis, G. A. and Agha, B. J., Eds., Lexington, (1987) pp. 392–401.

Simonelli et al. "Dissolution Rates of High Energy Polyvinylpyrrolidone (PVP)-Sulfathiazole Coprecipitates", *J. Pharm. Sci.* (1969) 58:538–549.

Simonelli et al. "Dissolution Rates of High Energy Sulfathiazole-Povidone Coprecipitates II: Characterization of Form of Drug Controlling Its Dissolution Rate via Solubility Studies", *J. Pharm. Sci.* (1976) 58:355–361.

Mayersohn M. et al. "New Method of Solid-States Dispersion for Increasing Dissolution Rates", *J. Pharm. Sci.* (1966) 55:1323–1324.

Bird, K. D., "Editorial Review: The Use of Spermicide Containing Nonoxynol-9 in the Prevention of HIV Infection", *AIDS* (1991) 5:791–796.

Louv, W. C. et al. "A Clinical Trial of Nonoxynol-9 for Preventing Gonococcal and Chlamydial Infections", *J. Infect. Dis.* (1988) 158:518–523.

Niruthisard S. et al. "The Effects of Frequent Nonoxynol-9 Use on the Vaginal and Cervical Mucosa", *Sex. Transm. Dis.* (1991) 18:176–179.

LaRocca, R. et al. "Microbiology of Povidone-Iodine—An Overview", *Proceedings of the International Symposium on Povidone,* Digenis, G. A. and Ansell, J., Eds. Lexington, (1983) pp. 101–119.

Winicov, M. et al. "New Low Iodine Products Based on Stabilized Povidone-Iodine Solution", *Proceedings of the International Suymposium on Povidone,* Digenis, G. A. and Ansell, J., Eds. Lexington, (1987) pp. 57–64.

Digenis, G. A. et al. "Studies on the Association of $^{14}$C-Povidone-$^{131}$I-Iodine Complex with Red Blood Cells and Bacterial Membranes", *Proceedings of International Symposium on Povidone,* Digenis, G. A. and Ansell, J., Eds. Lexington, (1983) pp. 302–311.

Ben-David A. et al. "The Protective Effect of Polyvinylpyrrolidone and Hydroxyethyl Starch on Noncryogenic Injury to Red Blood Cells", *Cryobiology* (1972) 9:192–197.

Berkelman, R. L. et al. "Increased Bactericidal Activity of Dilute Preparations of Povidone-Iodine Solutions", *J. Clin. Microbiol.* (1982) 15:635–639.

Polsky, Bruce, et al. "In Vitro Inactivation of HIV-1 by Contraceptive Sponge Containing Nonoxynol-9", *Lancet,* (1988) 1456.

HIGH ENERGY COPRECIPITATE OF NONOXYNOL OLIGOMER, PVP AND IODINE HAVING CONTRACEPTIVE AND POTENT ANTI-HIV PROPERTIES

TECHNICAL FIELD

The present invention relates to a composition which is a contraceptive with potent anti-HIV activity. The composition is a high energy coprecipitate of nonoxynol oligomers, polyvinylpyrrolidone (PVP) and iodine and shows a pronounced synergistic effect between the compounds of the composition.

BACKGROUND

Nonoxynol or nonylphenol(polyethoxy)ethanol is a nonionic surfactant used as the active ingredient in the majority of the commercially available spermicides. It inhibits the in vitro growth of venereal pathogens (see Benes, S. et al., (1985) *Antimicrob. Agent Chemother.* 27: 724–726; Kelly, J. P. et al., (2985), *Antimicrob. Agent Chemother* 27: 760–762; Austin, H., et al., (2984) *JAMA,* 251: 2822–2824; and Singh, B. et al., (1972) *Br. J. Vener. Dis.* 48: 57–64), including the herpes simplex viruses (see Asculai, S. S. et al., (1978) *Antimicrob. Agent Chemother.* 13: 686–690; Hicks, D. R., (1985) *Lancet,* 1422–1423; Friedman-Kein, (1986) *J. Am. Acad. Dermol.* 15: 989–994; Rapp, R. et al., (1985) *Antimicrob. Agent Chemother.* 28: 449–451; Voeller, B., (1986) *Lancet,* 1153; Malkovsky, M. et al., (1988) *Lancet,* 645; and Barbi, M. et al., (1987) *Boll. 1st. Sieroter.* (Milan) 66: 158–160).

By the nature of its synthesis, the nonoxynol-9 (N-9) (Igepal CO-630) derivative of nonoxynol is a polymer consisting of at least 17 oligomers of varying ethylene oxide (EO) chain length. The molecule of N-9 contains a hydrophobic moiety (nonylphenol portion) and a hydrophilic chain composed basically of ethylene oxide units. The compound is a product of a statistical polymerization reaction of 9 moles of ethylene oxide and one mole of nonylphenol (see equation below):

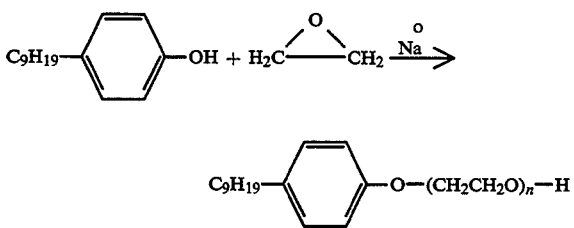

where "n" represents the number of ethylene oxide units.

The above reaction does not yield a distinct compound but a mixture of oligomers with different molecular weights. The physical and chemical characteristics of these oligomers change as a function of the varying molecular weight. (See Liebert, M. A., (1983) *J. Am. Coll. Toxicol.* 2: 35–60). As the length of the EO chain increases, the oligomers increase in water solubility. Nonoxynol-9 oligomers 1 through 6 (n=1–6) are considered oil soluble compounds, whereas the oligomers with a longer EO chain are soluble in water and polar organic solvents (see Liebert, supra).

These differences in chemical properties of N-9 oligomers affect their biological behavior both in vitro and in vivo. For instance, it was noted that the dermal toxicity of nonoxynol decreases as the molecular weight increases (see Liebert, supra) and that smaller molecular weight nonoxynol may be more toxic to fibroblasts than the larger ones (see Chvapil, M. et al., (1980) *Fertil. Steril.* 33: 521–525).

The in vitro spermicidal activity of the N-9 surfactant is also related to its molecular weight. Thus the oligomer n=9 when separated from the N-9 compound, was much more effective in inhibiting the motility of the spermatozoa than the higher molecular weight nonoxynols where n =30, 50, and 100. (See Chvapil, M. et al., (1980) *Fertil. Steril.* 33: 521–525.) The lower molecular weight nonoxynols (n=1 or 4) could not be studied appropriately because of their poor solubility in the aqueous testing medium (see Chvapil, supra).

Analogous dependence on molecular weight was observed in vivo. Oral absorption studies in the rat indicated that increasing the length of the ethylene oxide chain decreased N-9 oligomer intestinal absorption (see Knaak, J. B. et al., (1966) *Toxicol. Appl. Pharmacol.* 9: 331–340). Furthermore, data showed that absorption of N-9 through the vaginal membrane was poor and reflects the preferential absorption of lyophilic low molecular weight oligomers. (See Walter, B. A. et al. (1988) *Toxicol. Applied Pharmacol.* 96: 258–268.)

An efficient high pressure liquid chromatography (HPLC) method for the separation of [$^{14}$C]N-9 and characterization of the oligomeric components of the spermicide N-9 has been developed. (See Walter, B. A. et al. (1988) *Toxicol. Applied Pharmacol.* 96: 258–268; and Walter, B. A. et al., (1991) *Pharm. Res.* 8: 409–411).

Utilizing this normal phase gradient elution HPLC method, at least seventeen oligomers were isolated from commercial N-9. Selected oligomers representing the high, medium and low molecular weight fraction of N-9 were separated in milligram quantities by normal phase gradient HPLC (see Waiter, B. A. et al., (1991) *Pharm. Res.* 8: 409–411; and Walter, B. A. et al., (1991) *Pharm. Res.* 8: 403–408).

Polyvinylpyrrolidone (also known as povidone USP) is one of the most highly utilized polymers in medicine because of its safety for human use and unique hydrophilic properties (see Robinson, B. V. et al. (1990), *A critical review of the Kinetics and Toxicology of Polyvinylpyrrolidone,* Lewis Publishers, Inc., Michigan).

Discovered and used during World War II as a plasma expander, PVP is currently used as excipient in many pharmaceutical preparations intended for external use (e.g. povidone-iodine USP solutions such as Betadine); for oral use, such as a solubilizing agent and tablet disintegrant, and fox vaginal use such as in PVP-I douche.

Several studies have focused on the dissolution rate behavior of drug-povidone coprecipitates. (See Higuchi, W. I. et al., (1983) in *Proceedings of the International Symposium on Povidione,* Digenis, G. A. and Arisell, J., Eds. Lexington, pp. 71–79; Simonelli, A. P. et al., (1987) in *Proceedings of the 2nd International Symposium on Povidone,* Digenis, G. A. and Agha, B. J., Eds., Lexington, pp. 392–401; Simonelli et al., (1969) *J. Pharm. Sci.,* 58: 538–549; Simonelli et al. (1976) ibid. 65: 355–361.)

These studies found that the preferential dissolution of one component (hydrophilic polymer, such as PVP) can enhance the dissolution of the other component in a coprecipitate.

Drug/PVP high energy coprecipitates can be described as a drug incorporated into a solid PVP solution. Drug release from PVP coprecipitates are shown to follow dissolution kinetics of the polymer carrier of PVP provided that the PVP solvent uptake or swelling proceeds freely without inhibition by the drug.

Mayersohn and Gibaldi (Mayersohn M. et al., (1966) J. Pharm. Sci. 55: 1323-1324) showed greatly enhanced dissolution of the antibiotic griseofulvin when the drug was coprecipitated with povidone (PVP). Higuchi et al. investigated a povidone/sulfathiazole system and suggested that the resultant enhanced aqueous solubility of sulfathiazole was due to a high energy state of the drug in the PVP coprecipitate resulting in a supersaturated form of the drug after introduction into aqueous media. (See Higuchi, W. I. et al., (1983) in Proceedings of the International Symposium on Povidone, Digenis, G. A. and Ansell, J., Eds. Lexington, pp. 71-79.)

Simoneill et al., envisioned a PVP/drug coprecipitate model consisting of two components including the drug in amorphous state and PVP. (Simonelli, A. P. et al., (1987) in Proceedings of the 2nd International Symposium on Povidone, Digenis, G. A. and Agha, B. J., Eds., Lexington, pp. 392-401; Simonelli et al., (1969) J. Pharm. Sci. 58: 538-549; Simonelli et al. (1976) ibid. 65: 355-361.)

The in vitro spermicidal activity of three molecular weight fractions of N-9 were compared to that of N-9, using rabbit spermatozoa, at equimolar concentrations. nonoxynol-9/PVP complexes were found to be far more effective in immobilizing the sperm than either N-9 alone or in the separate fractions (Walter, B. A. et al., (1991) Pharm. Res. 8: 403-408).

The spermicidal activities of three oligomeric fractions of N-9 with human sperm have been assessed. Equimolar concentrations of three different molecular weight fractions of N-9 coprecipitated with PVP were used. These equimolar concentrations were 166 $\mu$g/ml for high molecular weight (HMW), (MW=599), 123 $\mu$g/ml for middle molecular weight (MMW>(MW=499) and 85 $\mu$g/ml for low molecular weight (LMW) (MW=306) N-9 fractions. The order of efficacy in immobilizing the human spermatozoa was HMW(MW=599)>MMW(MW=499)>LMW(MW=306) with complete sperm immobilization observed with PVP coprecipitated with N-9 HMW within 4.0 minutes and PVP coprecipitated with N-9 MMW within 15 minutes after exposure. Furthermore, addition of the spermicides interfered with the progressive motility and linearity of the sperm swimming pattern. PVP and buffer controls showed no decline in percentage motility over the course of the test.

Chvapil et al. recognized that the n=9 oligomeric fraction of nonoxynol-9 was more effective in inhibiting the motility of spermatozoa than the higher molecular weight nonoxynols. Chvapil et al., however, were unable to study the lower molecular weight oligomers (n=1-4) because of their poor solubility in aqueous media.

In contrast, however, Walter et al. were able to solubilize the water insoluble lower molecular weight N-9 oligomers by complexing them with the hydrophilic polymer polyvinylpyrrolidone (PVP). (See Walter, B. A. et al., (1991) Pharm. Res. 8: 403-408.)

The resulting high energy coprecipitate complexes of the low molecular species of N-9 were found to be at least effective spermicides at all concentrations tested when compared to their counterparts that were prepared from higher molecular weight N-9 oligomeric fractions. However, they were themselves effective spermicides. The above findings concluded that when N-9 is coprecipitated with PVP its spermicidal activity is enhanced. While PVP alone has no inherent sperm toxicity, the formation of N-9/PVP complexes seem to produce a synergistic response which causes a more rapid damage to the sperm than any of the two materials alone (Walter, B. A. et al., (1991) Pharm. Res. 8: 403-408).

Nonoxynol-9 (N-9) has been shown to be useful in the prophylaxis against sexually transmitted diseases (STD). (See Bird, K. D., (1991) AIDS 5: 791-796; and Louv, W. C. et al., (1988) J. Infect. Dis. 158: 518-523).

More recently, this spermicide has been shown to be effective against cell-associated HIV at concentrations of $\geq$0.05% (v/v). (See Hicks, D. R. et al., (1985) Lancet, ii: 1422-1423; Vopeller, B., (1986) Lancet, i: 1153; and Malkovsky, M., Newell, A., Dalgleish, A. G., (1988) Lancet, i: 645).

Unfortunately, N-9 causes epithelial disruption of the cervix and vagina when administered in high doses and high frequency (see Niruthisard S. et al., (1991) Sex. Transm. Dis. 18: 176-179). Higher rates of new HIV infections were found in prostitutes who used N-9 at great frequencies (see Kreiss, J. et al., International Conference on AIDS, Montreal, June 1989 [Abstract MAO36]). This observation was attributed to the high incidence of genital ulceration caused by high doses of N-9, in this group of women. Thus, the above findings tend to suggest that novel spermicide formulations containing N-9 should be efficacious at the smallest possible doses so that the integrity of the vaginal epithelium is not compromised.

The antimicrobia properties of povidone-iodine (PVP-I), a complex of polyvinyl pyrrolidone and iodine, have been well documented. PVP-I solutions (10% w/v) USP are among the most widely utilized antimicrobial agents. A 10% (w/v) solution of PVP-I contains 1% (w/v) of available iodine ($I_2$). The microbiological potency of PVP-I arises from the elemental (diatomic) or free iodine ($I_2$) in solution. The significant characteristic of iodophores, such as PVP-I, is that they carry almost all of their iodine in a complexed form so that the amount of free iodine ($I_2$) is quite low and PVP-I serves as the iodine reservoir delivering the free iodine into the solutions. Thus, iodophors exhibit reduced irritation properties and are relatively non-toxic (see LaRocca, R. et al., (1983) in Proceedings of the International Symposium on Povidone, Digenis, G. A. and Ansell, J., Eds. Lexington, pp. 101-119).

Stable, sterile (0.2%) PVP-I compositions containing as little as 0.02% iodine have been shown to be useful in treating eye infections in humans. A level of 0.02% iodine obtained by diluting a commercial 10% PVP-I solution at 1:50 with saline solution, is generally considered to be optimum to maximize performance and minimize irritation (see Winicov, M. et al., (1987) in Proceedings of the International Symposium on Povidone, Digenis, G. A. and Ansell, J., Eds. Lexington, pp. 57-64).

Data has shown that with doubly labeled $^{14}$C-PVP-$^{131}$I solutions the amount of iodine delivered into gram positive and negative bacteria cultures was three times greater when the iodine was complexed with PVP, than from an equimolar solution of $^{131}I_3$—(Lugol's solution). (See Digenis, G. A. et al., (1983) in Proceedings of International Symposium on Povidone, Digenis, G. A. and Ansell, J., Eds. Lexington, pp. 302-311).

The hydrophilic polymer PVP acts as a delivery system for iodine probably due to the membrane seeking properties of this polymer. Ben-David and Gavendo have shown that PVP at 4.6% w/v concentrations protect red blood cells from osmotic fragility and mechanical injury. (See Ben-David A. et al., (1972) *Cryobiology*, 9: 192–197). These workers suggested that this effect is brought about by a "coating" or external interaction of PVP with cell membranes.

The membrane-seeking properties of PVP suggest that in addition to its contribution to the solubilization ability of N-9, the PVP polymer, via its cell-membrane coating properties, also provides vaginal and cervical surface coverage coating with N-9 and iodine over extended periods of time.

In addition to its antimicrobial properties, PVP-I has been shown to inactivate HIV. (See Kaplan, J. C. et al. (1987) *Infect. Control* 8: 412–424; and Harbison, M. A. et al., (1989) *J. Acquir. Immune Defic. Syndr.* 2: 16–20). The concentration of iodine used in Kaplan's studies was equal to 0.025% for 250 ppm of $I_2$.

A 0.02% w/v (200 ppm) solution of iodine is considered non-toxic and non-irritating and is used for treatment of eye infections in humans. (See Winicov, M. et al., (1987) in *Proceedings of the International Symposium on Povidone*, Digenis, G. A. and Ansell, J., Eds. Lexington, pp. 57–64). In fact, the increased bactericidal activity of dilute solutions of povidone-iodine (Betadine—10% w/v PVP-I) have recently been well documented. Betadine contains 10,000 ppm (or 10,000 $\mu g/ml$) of available iodine and is often irritating to the tissues and has an undesirable brown color. (See Berkelman, R. L. et al., (1982) *J. Clin. Microbiol.* 15: 635–639.) At concentrations of about 0.02% w/v of iodine, the undesirable brown color of iodine is not a problem since in dilute solutions the color is hardly seen and the amount of iodine is not irritating to tissues.

None of the prior research in this area recognized the synergistic anti-HIV result of all three compounds when formulated into a high energy coprecipitate.

Furthermore, spermicides containing nonoxynol-9 and polyvinylpyrrolidone or polyurethane are known.

U.S. Pat. No. 4,317,447 to Williams discloses a device for delivering a medicament to the vaginal cavity consisting of a molded sheath of a mixture of a polymeric material and a medicament. The medicament which is dispersed in the polymeric material can be nonoxynol-9. The polymer may be selected from modified cellulose, polyvinyl alcohol, polyvinylpyrrolidone, polyacrylic and ethylene oxide polymer. Williams does not disclose the use of PVP-I in combination with a nonoxynol-9.

U.S. Pat. No. 5,156,164 to LeVeen et al. discloses that iodine can be dissolved in alcohol containing nonoxynol in a complex with polyurethane. LeVeen et al. disclose that a polyvinylpyrrolidone-iodine complex has been effective in treating resistant vaginitis. LeVeen et al. do not disclose or suggest combining PVP-I with nonoxynol.

U.S. Pat. No. 5,070,889 to Leveen et al. discloses a contraceptive sponge and tampon made of polyurethane iodine complex. Leveen et al. teaches away from the use of povidone iodine or use as a contraceptive.

U.S. Pat. No. 5,073,365 to Katz et al. discloses clinical and personal care articles enhanced by lubricants and adjuvants. The devices can be made of polyvinylpyrrolidone or polyurethane interpolymers. The device may take the form of vaginal diaphragms, tampons, condoms or cervical caps. The medicament may be nonoxynol-9. Katz et al. disclose that the personal care articles may prevent the transmission of venereal diseases, possibly including AIDS.

U.S. Pat. No. 4,707,362 to Nuwayser discloses a sustained release composition made of synthetic polymers such as polyvinylpyrrolidone. The bioerodible material in one embodiment has been modified so that a spermicide such as nonoxynol-9 is slowly released. Nuwayser does not disclose PVP-I in combination with nonoxynol-9.

U.S. Pat. No. 4,954,351 to Sackler et al. discloses a method of producing standardized povidone-iodine preparations. The patent discloses that the povidone-iodine solution can be incorporated into a suppository with 0.1 to 10% by weight of povidone-iodine. Sacklet et al. do not disclose the use of povidone-iodine in combination with nonoxynol-9.

U.S. Pat. No. 4,297,341 to Waller et al. discloses that a water-soluble complex comprising polyvinylpyrrolidone and gossypol is an effective spermicide. The patent discloses that a PVP-gossypol combination when compared to a comparative example of nonoxynol-9 alone, exhibited equal or greater spermicidal properties. Waller does not disclose PVP-I in combination with nonoxynol-9.

U.S. Pat. No. 4,925,033 to Stoner et al. discloses a microbicidal cleanser/barrier kit. One method of the invention involves applying a solution of povidone-iodine (PVP-I) to vaginal sponges or condoms. In another embodiment the povidone-iodine active ingredient may be added to spermicidal birth control compounds. Stoner et al. disclose that nonoxynol-9 is a known spermicidal compound. Stoner et al. do not disclose or suggest the particular combination of components in the form of a high energy coprecipitate, nor that the compounds show a synergistic anti-HIV effect.

Heterosexual transmission of human immunodeficiency virus (HIV), the causative agent of AIDS, is a growing concern in the United States where 37% of AIDS cases are heterosexually transmitted, the majority being male-to-female. Moreover, the frequency of global heterosexual transmission is probably greater where it is estimated to exceed 60% of all AIDS cases.

It has been suggested that a major contributing factor to heterosexual transmission of HIV is the presence of cell-free virus and virus-infected cell (cell-associated virus in genital secretions. Thus, vaginal contraceptives which inactivate HIV should be an effective barrier to transmission.

There is a need in the pharmaceutical area for a a contraceptive with potent anti-HIV activity. Ideally, a contraceptive agent is needed that can:

1a) provide rapid spermicide delivery (within 30–60 seconds);
1b) provide long-actingspermicidal activity after a single application;
2) protect the user against HIV (AIDS) and other sexually transmitted diseases (STDs);
3) protect vaginal and cervical epithelia from irritation;
4) enhance penetration of spermicide into cervical mucus;
5) exhibit low systemic bioavailability (low absorption);
6) be pharmaceutically and cosmetically acceptable (e.g. a tablet or capsule are preferred, as suppositories, creams and gels appear not to be as attractive to young users).

The composition of the invention meets the above objectives and provides a high energy coprecipitate of nonoxynol-9 oligomers, polyvinylpyrrolidone and iodine (PVP-I). The composition shows a pronounced synergistic effect between the compounds which results in potent anti-HIV activity. The composition of the invention safely and cost-effectively provides a contraceptive with potent anti-HIV activity.

Disclosure of the Invention

It is an object of the invention to provide a novel and potent contraceptive and/or spermicide possessing pronounced anti-HIV properties which is a high energy coprecipitate composition comprising N-9 oligomers and PVP and iodine. The PVP and iodine ingredients may be present in the coprecipitate composition as the complex PVP-I.

The invention further provides a high energy coprecipitate composition which is in the form of a powder. In a preferred embodiment the invention provides a high energy coprecipitate composition including PVP-I which comprises about 0.09–9% w/w of iodine.

In yet another embodiment, the invention provides a high energy coprecipitate composition of N-9 complexed with PVP comprising an antiviral concentration of free iodine of about 0.03% w/v or about 300 ppm.

The invention additionally provides a high energy coprecipitate composition of N-9 complexed with PVP comprising an antiviral concentration of free iodine providing about 9.4 to 0.09 % $I_2$ providing an effective concentration of free iodine of 0.0094% w/v (94 ppm) and from about 11.8 –5.8% w/w of N-9 providing an effective concentration of N-9 of 0.0058% w/v (58 ppm).

In a further embodiment, the invention includes a high energy coprecipitate composition comprising an effective final concentration of from about 4–200 μg/ml of N-9.

The invention advantageously provides for a method of preparing a high-energy coprecipitate composition comprising the steps of:
(a) fractionating commercially available spermicide N-9 to seventeen oligomers by a preparative high pressure liquid chromatography (HPLC) procedure; and
(b) converting the oligomers or commercially available N-9 to a high energy coprecipitate with PVP and iodine.

Preferred is a method of preparing a high-energy coprecipitate composition including the steps of:
(a) fractionating commercially available spermicide nonoxynol-9 (N-9) to seventeen oligomers by high pressure liquid chromatography (HPLC);
(b) adding an N-9 oligomer obtained in step (a) with a 10% or 1% solution w/v of PVP-I in a solvent,
(c) placing the product of step (b) in an oil bath at about 100° C., and allowing the solvent to evaporate.
(d) obtaining a high energy coprecipitate of N-9, polyvinylpyrrolidone (PVP) and iodine.

Also included is a method of treating a female comprising administering to a female an effective amount of a high energy coprecipitate comprising N-9 oligomers, PVP and iodine to achieve a contraceptive and anti-HIV environment in the vaginal cavity. Thus, the invention provides spermicidal and anti-HIV activity with no irritation to the cervical and vaginal epithelia, and may take the form of an elegant, free flowing powder.

DESCRIPTION OF THE INVENTION

The present invention describes methodology for the preparation and assessment of new chemical entities with pronounced spermicidal and anti-HIV properties. These chemical entities incorporate N-9 or selected N-9 oligomers, small amounts of iodine ($I_2$) and the hydrophilic polymer PVP in such a way as to form high energy complexes, also known as coprecipitates.

The novel contraceptive composition of the invention comprises a high energy coprecipitate made from N-9 oligomers, PVP and iodine. A pronounced synergistic effect is obtained between the compounds, enhancing the anti-HIV activity of the compounds when in the form of a coprecipitate. Due to the synergistic effect of the compounds present in the high energy coprecipitate, the coprecipitate requires less of each of the individual ingredients to achieve the desired anti-HIV result, than if the compounds were to be administered as a mixture. This is beneficial as it reduces irritation to tissues caused by higher doses of N-9 and iodine and thus reduces the potential for HIV virus transmission.

The high energy coprecipitates of the invention are formulated by fractionating commercially available spermicide, N-9, into seventeen oligomers by a preparative high pressure liquid chromatography (HPLC) procedure. Selected oligomers of N-9, or the commercially available N-9, are converted to high energy coprecipitates with PVP and various amounts of iodine (PVP-I). In a preferred embodiment the amount of iodine is about 0.09–9% w/w of iodine. The content of N-9 in the above complexes, in a preferred embodiment, ranges from 5.8–12% w/w.

N-9 and its oligomeric components are inherently viscous liquids which are converted to free flowing, water soluble powders by forming coprecipitates with PVP-I. Several combinations of iodine ($I_2$), N-9 and PVP are utilized to produce powders which exhibit a variety of spermicidal and anti-HIV activities.

In order to test and compare the anti-HIV activity of the high energy coprecipitates of the invention, the following assay procedure was performed.

Procedure for Anti-HIV Activity Assessment

High-titer suspensions (>$10^6$ infectious particles/ml) were incubated with each compound for 5 seconds, then immediately diluted 1:50 onto cultures of human MT-2 cells for detection of infectivity. Cellular toxicities were observed and no antiviral activities were expected after the 1:50 dilution, hence all antiviral activity would have resulted from the 5 second exposure. Infections were monitored by syncytium (giant cells) formation and Immune Fluorescence Assay (IFA). This assay utilizes all antiviral antibody with a fluorochrome attached to it through a covalent bond. Virus particles get to fluoresce when viable, and therefore the degree of infectivity is quantitated.

The results after 3, 5 and 8 days of incubation are shown in Table 1. In the control experiment, using the untreated virus, the MT-2 cells are 100% infected at the end of 3 days.

A 1% value or less, indicates a complete inactivation of the virus as measured by the IFA method, i.e. no fluorescent particles of the virus exist inside or outside the cells (Table 1).

Syncytia (giant cell) formation is assessed by staining techniques with subsequent microscopic examination. Syncytia formation indicates invasion of the MT-2 cells by the virus.

The method described is that of Montefiori et al. "Evaluation of Antiviral Drugs and neutralizing antibodies to human immunodeficiency virus by a rapid and sensitive microtiter infection assay", *J. Clin. Microbiol.* 1988, Vol 26: 231–235, incorporated herein by reference.

Table 1 summarizes the results of anti-HIV activity assessment of two high energy coprecipitate powders of PVP-I and N-9. The first was made with oligomers of N-9 with an average molecular weight of 599 and the second with the oligomers of N-9 with an average molecular weight of 306. Both samples were coprecipitated with PVP, iodine and one of N-9 oligomers mentioned above.

TABLE 1

Inactivation of Cell-Free and Cell-Associated HIV-1[1]

| DRUG | 3 days | | 5 days | | 8 days |
|---|---|---|---|---|---|
| | Syncytia | IFA[2] | Syncytia | IFA | IFA |
| PVP (11.8 mg/ml) | +++ | >80% | CPE[3] | CPE | CPE |
| PVP (0.236 mg/ml) | +++ | >80% | CPE | CPE | CPE |
| PVP (3.24 mg/ml) high MW N-9 (0.2 mg/ml) | — | 10% | +++ | >80% | CPE |
| PVP (0.0648 mg/ml) high MW N-9 (0.004 mg/ml) | +++ | >80% | CPE | CPE | CPE |
| PVP (5.8 mg/ml) low MW N-9 (0.2 mg/ml) | — | 10% | +++ | >80% | CPE |
| PVP (0.116 mg/ml) low MW N-9 (0.004 mg/ml) | +++ | >80% | CPE | CPE | CPE |
| PVP-I (11.8 mg/ml) | — | >1% | — | >1% | 0% |
| PVP-I (0.236 mg/ml) | +++ | >80% | CPE | CPE | CPE |
| PVP-I (3.24 mg/ml) high MW N-9 (—) (0.2 mg/ml) | +++ | <1% | — | <1% | 0% |
| PVP-I (0.0648 mg/ml) high MW N-9 (0.004 mg/ml) | +++ | >80% | CPE | CPE | CPE |
| PVP-I (5.8 mg/ml) low MW N-9 (0.2 mg/ml) | +++ | >80% | CPE | CPE | CPE |
| PVP-I (5.8 mg/ml) low MW N-9 (0.2 mg/ml) | — | <1% | — | <1% | 0% |
| PVP-I (0.116 mg/ml) low MW N-9 (0.004 mg/ml) | — | >80% | CPE | CPE | CPE |
| +++ | | | | | |

[1]Details of experimental procedures are given in the test.
[2]% IFA positive cells
[3]CPE, viral-induced cytopathic effect was complete.
HMW N-9 = 599
LMW N-9 = 306

The data in Table 1 show that PVP-I at a concentration of 11.8 mg/ml completely inactivated cell-free and cell-associated HIV-1. This represents approximately an effective concentration of 1.2% w/v of PVP-I or 0.12% w/v of free iodine (or 1,200 ppm of $I_2$).

A solution was made from a PVP-I and N-9 high energy coprecipitate. The coprecipitate composition was 94.2% w/w of PVP-I and 5.8% w/w of N-9, at a concentration of 3.24 mg/ml of PVP-I and 0.2 mg/ml of N-9 of an average molecular weight of 599. This composition achieved a complete eradication of the HIV virus in 30 seconds.

The use of high molecular weight N-9 oligomers as a component of the anti-HIV coprecipitate composition decreases the systemic absorption of N-9 and therefore N-9 is localized in the vagina and less toxic to the female.

Similar anti-HIV results were obtained with a coprecipitate of about 5.8 mg/ml PVP-I and about 0.2 mg/ml N-9 of an average molecular weight of 306. These results represent an antiviral concentration of free iodine of about 0.03% w/v (324 ppm). This level of iodine is not irritating to the vaginal epithelial tissue and desirably has no noticeable brown color.

In contrast to the above results, when no iodine is present in a coprecipitate composition made with 94.2% w/w of PVP and 5.8% w/w of N-9, at a concentration of 3.24 mg/mL of PVP and 0.2 mg/mL of N-9 of an average molecular weight of 599, the antiviral properties of the product were substantially reduced (see Table 1).

A similar reduction of the antiviral properties was also observed when the product was made from a PVP/N-9 high energy coprecipitate of 94.2% w/w of PVP and 5.8% w/w of N-9, at a concentration of 3.24 mg/mL of PVP and 0.2 mg/mL of N-9 of an average molecular weight of 599 (see Table 1).

Thus, in a preferred embodiment, the presence of 324 ppm iodine in the case of high molecular weight (599) N-9 and 580 ppm of iodine, in the case of the lower molecular weight N-9 (306) importantly adds to the synergistic anti-HIV effect of the high energy coprecipitate. The iodine and N-9 both act in a synergistic manner when complexed with PVP.

Other solutions made from PVP-I and N-9 coprecipitate in accordance with the invention include 94.2% of PVP-I and 5.8% of N-9 with an average molecular weight of 599. A further solution made from PVP-I and N-9 coprecipitate comprises 94.2% of PVP and 5.8% of N-9 with a weight average molecular weight of 306.

The chemical union of the iodine, PVP and several oligomers of the spermicidal agent N-9 with different molecular weights results in an impressive synergistic action of iodine and the spermicide N-9 against human immunodeficiency virus (HIV) (Tables 1 and 2).

The coprecipitate of the invention shows that the synergism between iodine and N-9 is of such magnitude that solutions with even smaller concentrations of these species can be used. Again, this is beneficial as it reduces vaginal irritation and thus reduces the potential for HIV virus transmission. Indeed, a complete eradication of the HIV-virus was obtained when coprecipitates of PVP, iodine and N-9 solution, containing as low as 58 ppm of N-9 and 940 ppm of PVP-I (94 ppm of iodine), were utilized (see Table 2).

TABLE 2

| Concentration on Virus | | |
|---|---|---|
| [μg/mL = ppm] | Syncytia | IFA Position |

TABLE 2-continued

| Compound | N9 | PVP-I | % | Cells % |
|---|---|---|---|---|
| No drug | — | — | 100 | 100 |
| KY048 | 58 | 940 | 0 | 0 |
| KY050 | 117.4 | 10 | 10 | 5 |
| KY052 | 118 | 0 | 30 | 10 |

Composition of KY Coprecipitates

| | PVP | | PVP-I | | $I_2$ | | N-9 | |
|---|---|---|---|---|---|---|---|---|
| | % | ppm | % | ppm | % | ppm | % | ppm |
| KY048 | 0 | 0 | 94.20 | 940,000 | 9.40 | 94,000 | 5.80 | 58,000 |
| KY050 | 88.58 | 885,800 | 0.90 | 9,400 | 0.09 | 940 | 10.52 | 105,200 |
| KY052 | 88.20 | 882,000 | 0 | 0 | 0 | 0 | 11.8 | 118,000 |

The synergistic effect against the HIV is so significant that the above PVP-I/N-9 solution at concentrations as small as 58 ppm of N-9 and 94 ppm of iodine are effective, against the HIV virus (Table 2).

In addition to the unexpected synergism between the compounds, the coprecipitation of iodine, N-9 and PVP results in the formation of freely flowing powders which enable the preparation of elegant solid pharmaceutical formulations with control release properties. The coprecipitate powders are particularly useful in the design of acceptable solid formulations intended for vaginal, or other appropriate use.

The coprecipitate composition may be administered in the form of solid formulations, such as tablets or capsules, or as ointments, creams or suppositories. In a preferred embodiment the composition is administered in the form of a capsule or tablet.

Tablets, capsules, ointments, creams or suppositories may be formulated according methods known in the art such as those disclosed in Remington's Pharmaceutical Science, 18th Ed. pp. 1602-1712, incorporated herein by reference.

In contrast, N-9 by itself is a viscous liquid which cannot be formulated as a powder in solid dosage forms such as tablets or capsules. N-9 has heretofore been unable to form elegant tablets or capsules which are preferred by the user cover creams and suppositories. Additionally, at its generally accepted effective spermicidal concentrations (approximately 160 mg/ml), N-9 is irritating to the vaginal epithelia and lining of the vaginal vault.

At concentrations below 550 ppm neither iodine nor N-9 are known to irritate sensitive membrane linings of the human body. Thus, the coprecipitate powders can be formulated into drug delivery systems that can release their active ingredients in a predictable manner without causing irritation to surrounding membrane linings.

The powders of the invention are acceptable to the user and furnish prolonged protection against AIDS and sexually transmitted diseases (STDs) with minimal absorption to the systemic circulation.

The main ingredient in the powders of the high energy coprecipitates, described in this invention, is the hydrophilic polymer PVP. This polymer, which exists in the powders in a ratio of approximately forty parts to one part of N-9, not only enhances the solubility of the various N-9 oligomers but also contributes to the synergistic action of N-9 and iodine against the AIDS virus. Thus, in a most important aspect of the invention, the active ingredients (N-9 and iodine) are present in the powder in such minuscule quantities that are known not to irritate membrane linings of the body.

The following examples are given to illustrate the invention, but are not to be construed as limiting.

EXAMPLE 1

The various compositions of coprecipitates are made according to the following general procedure: Stock solutions of approximately 1% w/v of PVP-I and 1% w/v N-9 are made in ethanol or methanol.

The N-9 stock solution is added dropwise to an aliquot of the PVP-I stock solution with stirring. It is critical that the two solutions are mixed at a very slow rate. Thus, the introduction of the N-9 solution, into the round bottom flask, containing the PVP-I, must be done dropwise but over a period of not longer than 1.5 hours.

Subsequently, the solvent is evaporated from the PVP-I/N-9 solution by heating in a preheated oil bath at 100° C. The temperature must be kept constant at 100° C. The evaporation process should last between 1-2 hours but no longer than two hours.

EXAMPLE 2

If a "glassy" coprecipitate is obtained following the general procedure described in example 1, diethyl ether is mixed with the residue. Upon evaporation of the diethyl ether a crystalline powder is obtained.

EXAMPLE 3

If a finely divided crystalline powder of the PVP-I/N-9 coprecipitate is desired, following the procedure described in Example 1, the residue, received after evaporation described in Example 1, is dissolved in a mixture of methanol/1,4 dioxane (1:4 ratio v/v) and subjected to freeze-drying for at least 12 hours. A fine crystalline powder is obtained by the freeze-drying step.

EXAMPLE 4

Commercially available nonoxynol-9 containing seventeen oligomers with an average molecular weight of 599 is utilized as a component in the general procedure described in Example 1. The oligomer of N-9 is isolated by the HPLC procedure disclosed in Walter, B. A. et al. (1988) Toxicol. Applied Pharmacol. 96: 258-268; Walter, B. A. et al., (1991) Pharm. Res. 8: 409-411; and Walter, B. A. et al., (1991) Pharm. Res. 8: 403-408, incorporated herein by reference).

Briefly, the separation is achieved by a preparative Zorbax-NH$_2$ column (250 mm, 7 µm, ×21.1 mm i.d.).

EXAMPLE 5

Stock solutions of N-9 (250 mg/ml) were prepared in tetrahydrofuran. A 1.0 ml aliquot was separated on a preparative Zorbax-NH$_2$ 7 µm column, 250 mm×21.2 mm I.D., using a linear solvent gradient from 98% A-2% B to 50% A-50% B in 90 min., where A=tetrahydrofuran:hexane (20:80, v/v) and B=water:2-propanol (10:90, v/v) delivered at 9.9 ml/min at ambient temperature and detection at 280 nm. The HPLC system used was a Waters HPLC system (Millipore, Waters Chromatography Division, Millford, Mass.) consisting of two Waters Model 510 HPLC pumps, a Waters Model 680 gradient controller, a Waters Model 440 Absorbance detector (280 nm), and a Waters Model SE120 dual channel recorder. Samples were introduced via a Rheodyne Model 7125 loop injector equipped with a 100 μl loop onto the HPLC column. Seventeen oligomers were collected, concentrated and reinjected onto the analytical system for further purification. The 599 molecular weight fraction and 305 molecular weight fraction were separated from the other fractions.

A 10% or 1% solution of w/v of PVP-I and the MW 599 fraction of the compound of nonoxynol-9 (N9) (isolated as set forth above) in absolute ethanol (methanol) was made. Both solutions were added via dropping funnels into a round bottom flask. It is important in this step to allow the dropping of the two solutions to continue for 1.5 hours. Thus the addition of the two solutions must take place slowly.

To an oil bath which had been preheated to 100° C., the flask was placed and the solvent allowed to evaporate. It was important to make sure that the temperature was well controlled during the evaporation process. The evaporation process should take between 1 and 2 hours. The evaporation should not take place longer than 2 hours.

A high energy coprecipitate of the compounds is obtained.

Examples 6-8 show formulations of the high energy coprecipitate of the invention.

EXAMPLE 6

A high energy coprecipitate composition of 9.4-0.09% I w/w and 11.8-5.8% N-9 w/w. The high energy coprecipitate provides anti-HIV protection at an effective concentration of about 3.24 mg/mi of PVP-I and 0.2 mg/ml of N-9 of an average molecular weight of 599 in a tablet formulation.

EXAMPLE 7

A high energy coprecipitate providing anti-HIV protection at an effective concentration of about 5.8 mg/ml PVP-I and 0.2 mg/ml N-9 of an average molecular weight of 305 in a capsule formulation.

EXAMPLE 8

A high energy coprecipitate providing anti-HIV protection at an effective concentration of about 58 ppm of N-9 and 940 ppm of PVP-I or 94 ppm of iodine in a cream formulation.

The invention is not to be limited to the exact details of operation, or to the exact compositions, methods, procedures or embodiments shown and described, as obvious modifications and equivalents will be apparent to one skilled in the art. The invention is therefore to be limited only by the full scope which can be legally accorded to the appended claims.

We claim:

1. A composition comprising a high energy coprecipitate of nonoxynol oligomer and polyvinylpyrrolidone polymer and iodine, or polyvinylpyrrolidone-iodine complex (PVP-I), wherein the combined effect of the compounds simultaneously precipitated in said high energy coprecipitate exceeds the individual effect of said compounds, and wherein said high energy coprecipitate has antiviral activity against human immunodeficiency virus-1 (HIV-1) in an MT-2 assay.

2. A composition according to claim 1, wherein said coprecipitate is a powder.

3. A composition according to claim 2, wherein said powder is a finely divided crystalline powder.

4. A composition according to claim 1, wherein said PVP-I comprises about 0.09-9.4% w/w of iodine.

5. A composition according to claim 1, wherein said PVP-I comprises an antiviral concentration of free iodine of about 0.03% w/v or 300 ppm complexed with PVP.

6. A composition according to claim 1, wherein said PVP-I comprises an effective antiviral concentration of free iodine of about 0.0094 w/v of iodine or 94 ppm complexed with PVP.

7. A composition according to claim 1, wherein said nonoxynol oligomer of said coprecipitate comprises from about 5.8 to 11.8% w/w of nonoxynol-9 oligomer.

8. A composition according to claim 1, wherein said coprecipitate is present at a concentration of about 3.24 mg/ml of PVP-I and about 0.2 mg/ml of N-9 oligomer of an average molecular weight of 599.

9. A composition according to claim 1, wherein said coprecipitate is present at a concentration of about 5.8 mg/ml PVP-I and about 0.2 mg/ml N-9 oligomer of an average molecular weight of 306.

10. A composition according to claim 1 wherein said coprecipitate is present at a concentration of about 5.8 ppm of N-9 oligomer and about 940 ppm of PVP-I or 94 ppm of iodine.

11. A composition of claim 1, wherein said nonoxynol oligomer is an nonoxynol-9 oligomer with an average molecular weight of 599.

12. A composition of claim 1, wherein said nonoxynol oligomer is nonoxynol-9 oligomer comprising oligomers of N-9 having a range of molecular weight of each oligomer from about 264 to about 1000.

13. A composition of claim 1, wherein the percent of polyvinylpyrrolidone ranges from about 88% to about 97%.

14. A composition of claim 1, wherein the average molecular weight of said polyvinylpyrrolidone ranges from about 2,500 to 1,100,000.

15. A method of preparing a composition according to claim 1, comprising the steps of:
 (a) fractionating commercially available spermicide nonoxynol-9 (N-9) to seventeen oligomers by high pressure liquid chromatography (HPLC);
 (b) adding an N-9 oligomer obtained in step (a) with a 10% or 1% solution w/v of PVP-I in a solvent,
 (c) placing the product of step (b) in an oil bath at about 100° C., and allowing the solvent to evaporate; and
 (d) obtaining a high energy coprecipitate of N-9, polyvinylpyrrolidone (PVP) and iodine.

16. A method of achieving a contraceptive and anti-HIV in environment the vaginal cavity of a female comprising administering to said vaginal cavity of said female an effective amount of a composition according to claim 1 to achieve a contraceptive and anti-HIV in environment the vaginal cavity of said female.

17. The method according to claim 16, wherein said coprecipitate is administered in a form selected from the group consisting of tablets, capsules, ointments, creams and suppositories.

18. The method according to claim 16, wherein said effective amount of said coprecipitate comprises from about 6-12% w/v N-9 and about 0.09-9% w/v of PVP-I.

* * * * *